(12) United States Patent
Hamilton

(10) Patent No.: US 11,883,547 B2
(45) Date of Patent: Jan. 30, 2024

(54) PAPER MONEY SANITATION APPARATUS

(71) Applicant: Russell Hamilton, College Station, TX (US)

(72) Inventor: Russell Hamilton, College Station, TX (US)

( * ) Notice: Subject to any disclaimer, the term of this patent is extended or adjusted under 35 U.S.C. 154(b) by 593 days.

(21) Appl. No.: 17/115,851

(22) Filed: Dec. 9, 2020

(65) Prior Publication Data

US 2022/0175985 A1 Jun. 9, 2022

(51) Int. Cl.
| | | |
|---|---|---|
| A61L 2/10 | (2006.01) | |
| G07D 11/14 | (2019.01) | |
| B65H 5/06 | (2006.01) | |
| A61L 2/26 | (2006.01) | |

(52) U.S. Cl.
CPC .................. *A61L 2/10* (2013.01); *A61L 2/26* (2013.01); *B65H 5/062* (2013.01); *G07D 11/14* (2019.01); *A61L 2202/11* (2013.01); *A61L 2202/121* (2013.01); *A61L 2202/122* (2013.01); *A61L 2202/26* (2013.01); *B65H 2701/1912* (2013.01); *G07D 2211/00* (2013.01)

(58) Field of Classification Search
CPC .......... A61L 2/10; A61L 2/26; A61L 2202/11; A61L 2202/121; A61L 2202/122; A61L 2202/26; G07D 11/14; G07D 2211/00; B65H 5/062; B65H 2701/1912
USPC ........................... 250/453.11, 454.11, 455.11
See application file for complete search history.

(56) References Cited

U.S. PATENT DOCUMENTS

| | | | |
|---|---|---|---|
| 4,449,050 A | 5/1984 | Kamhi | |
| 5,374,814 A | 12/1994 | Kako | |
| 9,415,124 B2 | 8/2016 | Back | |
| D767,667 S | 9/2016 | van Slooten | |
| 9,498,551 B2 | 11/2016 | Yanke | |
| 9,511,164 B2 | 12/2016 | Dayton | |
| 9,839,947 B2 | 12/2017 | Lawandy | |
| 2013/0045133 A1 | 2/2013 | Maguire | |
| 2022/0062472 A1* | 3/2022 | Owen | G07D 11/00 |

FOREIGN PATENT DOCUMENTS

WO WO2015194713 12/2015

* cited by examiner

*Primary Examiner* — Nicole M Ippolito

(57) ABSTRACT

A paper money sanitation apparatus for preventing the transmission of viruses includes a housing having an input slot and an output slot extending through to a housing cavity. A plurality of roller pairs is coupled within the housing cavity. Each roller pair has an upper roller bar and a lower roller bar positioned to have sufficient space to receive a banknote. A drive system is coupled to the plurality of roller pairs and powered by a motor to pull the banknote from the input slot and out the output slot. A battery is coupled to the housing and is in operational communication with the motor. A plurality of ultraviolet lights is coupled within the housing cavity to disinfect the banknote as it passes through.

11 Claims, 6 Drawing Sheets

PAPER MONEY SANITATION APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to banknote sanitizers and more particularly pertains to a new banknote sanitizer for preventing the transmission of viruses. The present invention includes an input slot and an output slot to facilitate the transfer of money from one party to another.

(2) Description of Related Art Including Information Disclosed Under 37 CFR 1.97 and 1.98

The prior art relates to banknote sanitizers. Known devices are often integrated into larger pieces of equipment such as money counters and cash registers. Existing devices typically only have a single access for placing notes and retrieving notes after cleaning.

BRIEF SUMMARY OF THE INVENTION

An embodiment of the disclosure meets the needs presented above by generally comprising a housing having a housing front side, a housing back side, a housing top side, a housing bottom side, a housing left side, and a housing right side defining a housing cavity. The housing has an input slot extending through to the housing cavity and the housing back side has an output slot extending through to the housing cavity. A plurality of roller pairs is coupled to the housing. Each roller pair comprises an upper roller axle extending between the housing left side and the housing right side within the housing cavity. An upper roller bar is coupled to the upper roller axle. A lower roller axle extends between the housing left side and the housing right side within the housing cavity vertically beneath the upper roller axle. A lower roller bar is coupled to the lower roller axle. The upper roller bar and the lower roller bar are positioned to have sufficient space to contactingly receive a banknote. A drive system is coupled to the plurality of roller pairs. The drive system is in operational communication with each of the upper roller axles and the lower roller axles to synchronize rotation thereof. A motor is coupled to the drive system and is in operational communication with the drive system to rotate the plurality of roller pairs. A power button s coupled to the housing and is in operational communication with the motor. A battery is coupled to the housing and is in operational communication with the motor. A plurality of ultraviolet lights is coupled to the housing. Each ultraviolet light is coupled within the housing cavity and is in operational communication with the battery.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
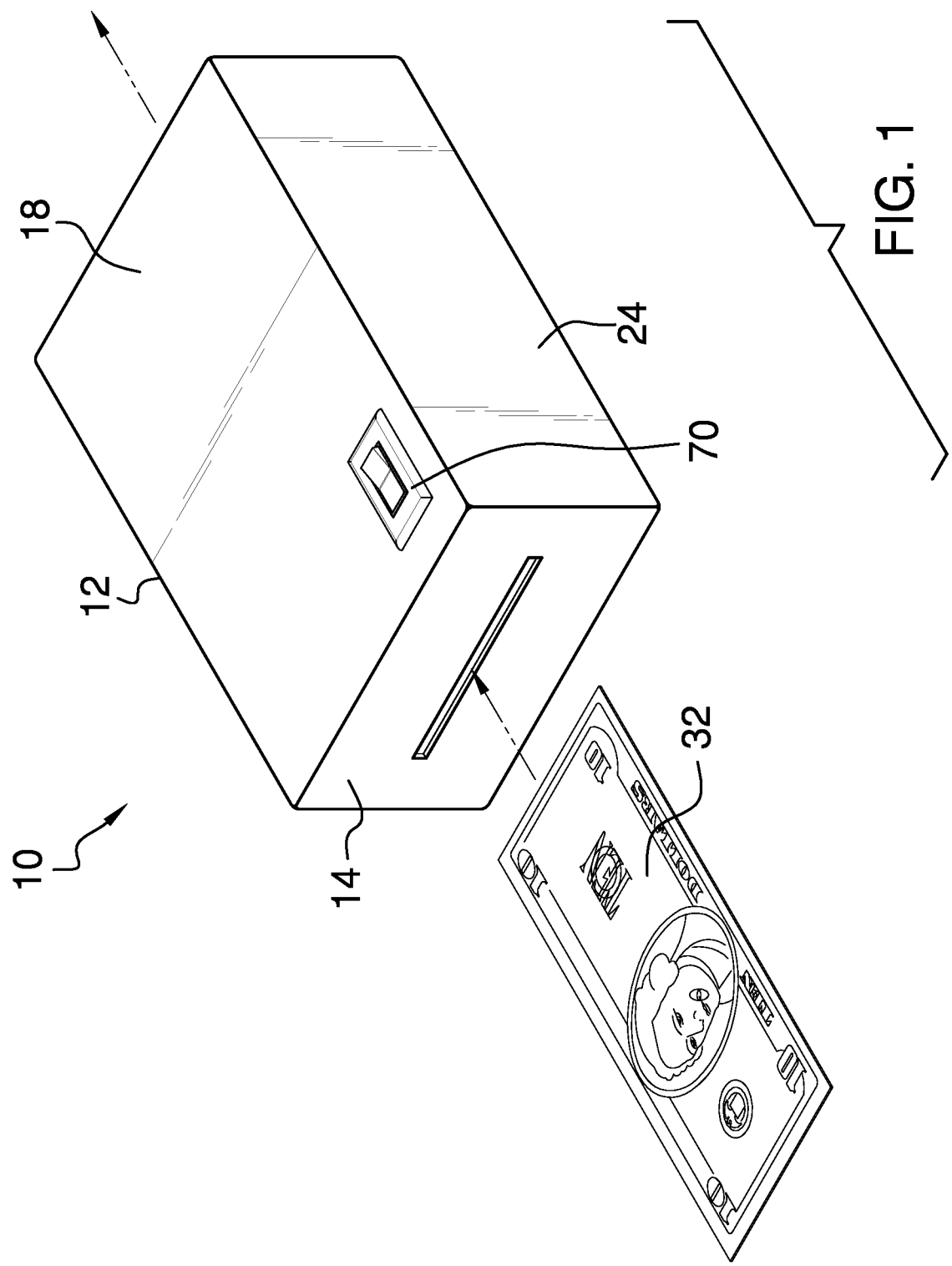
FIG. 1 is an isometric view of a paper money sanitation apparatus according to an embodiment of the disclosure.
Figure 2:
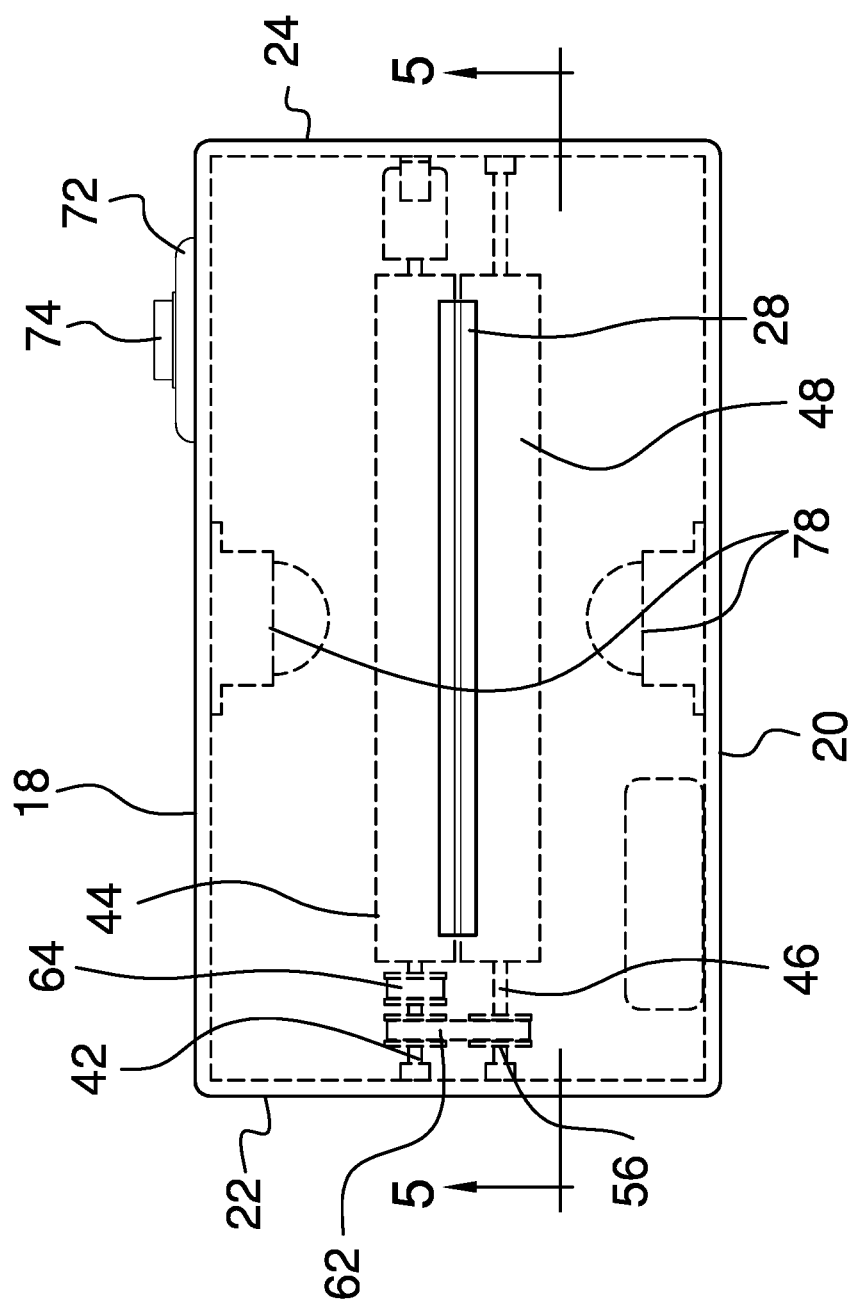
FIG. 2 is a front elevation view of an embodiment of the disclosure.
Figure 3:
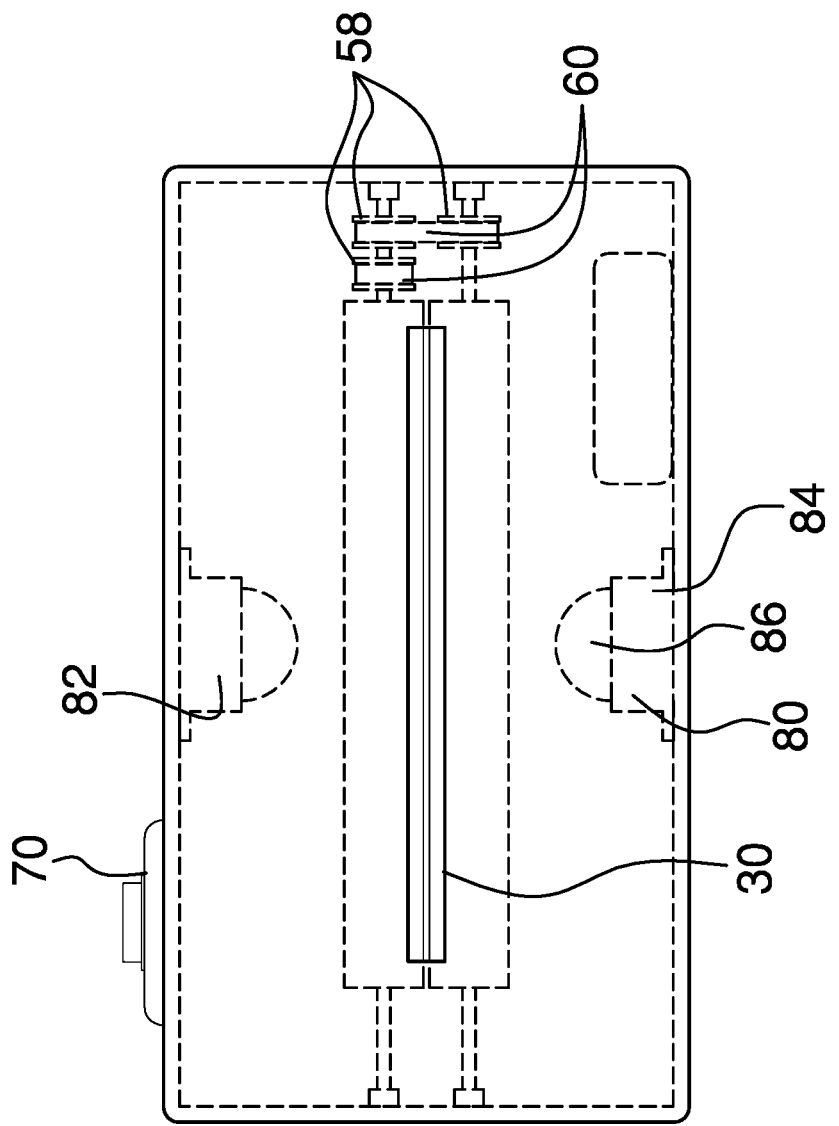
FIG. 3 is a rear elevation view of an embodiment of the disclosure.
Figure 4:
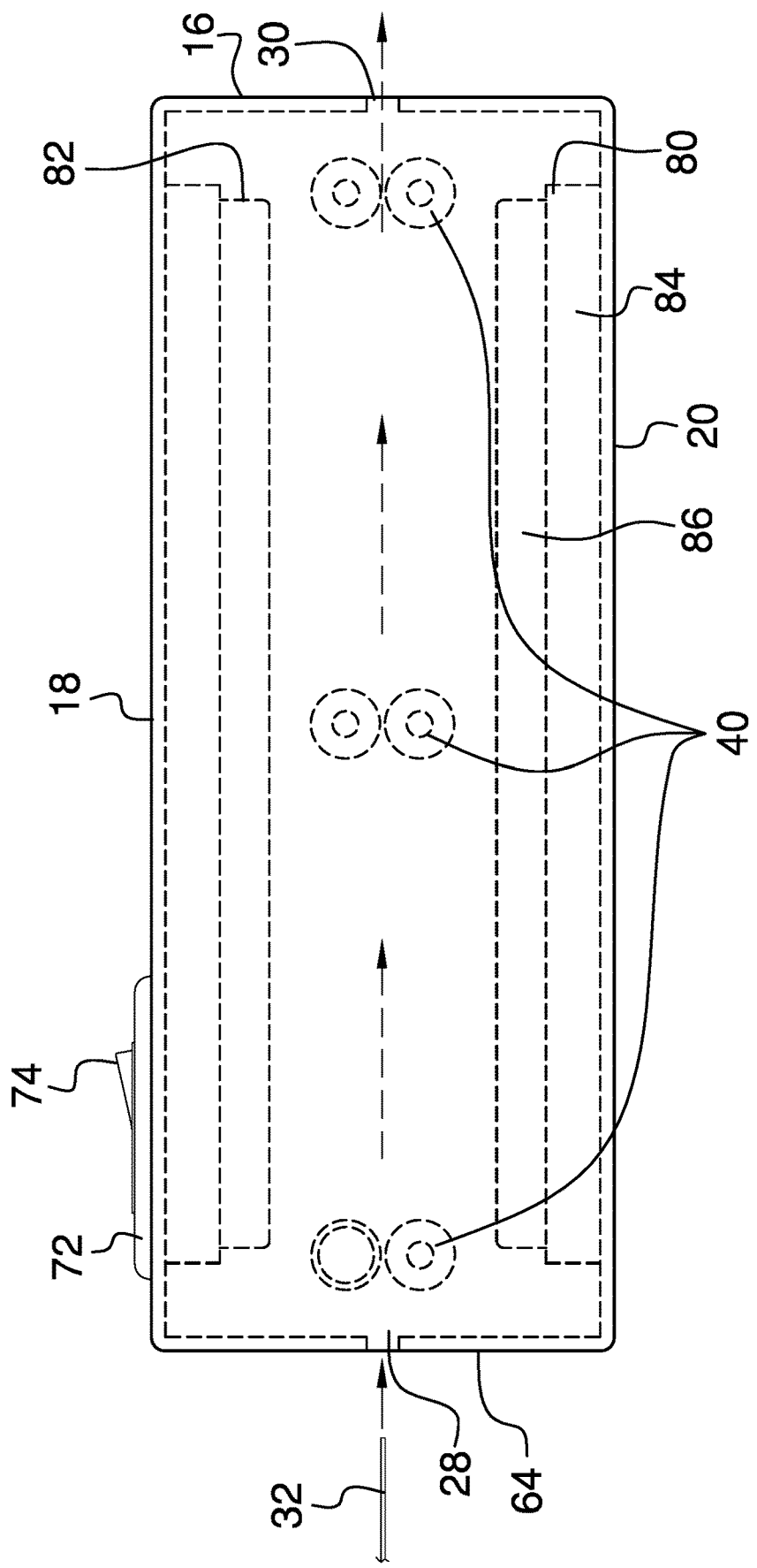
FIG. 4 is a side elevation view of an embodiment of the disclosure.
Figure 5:
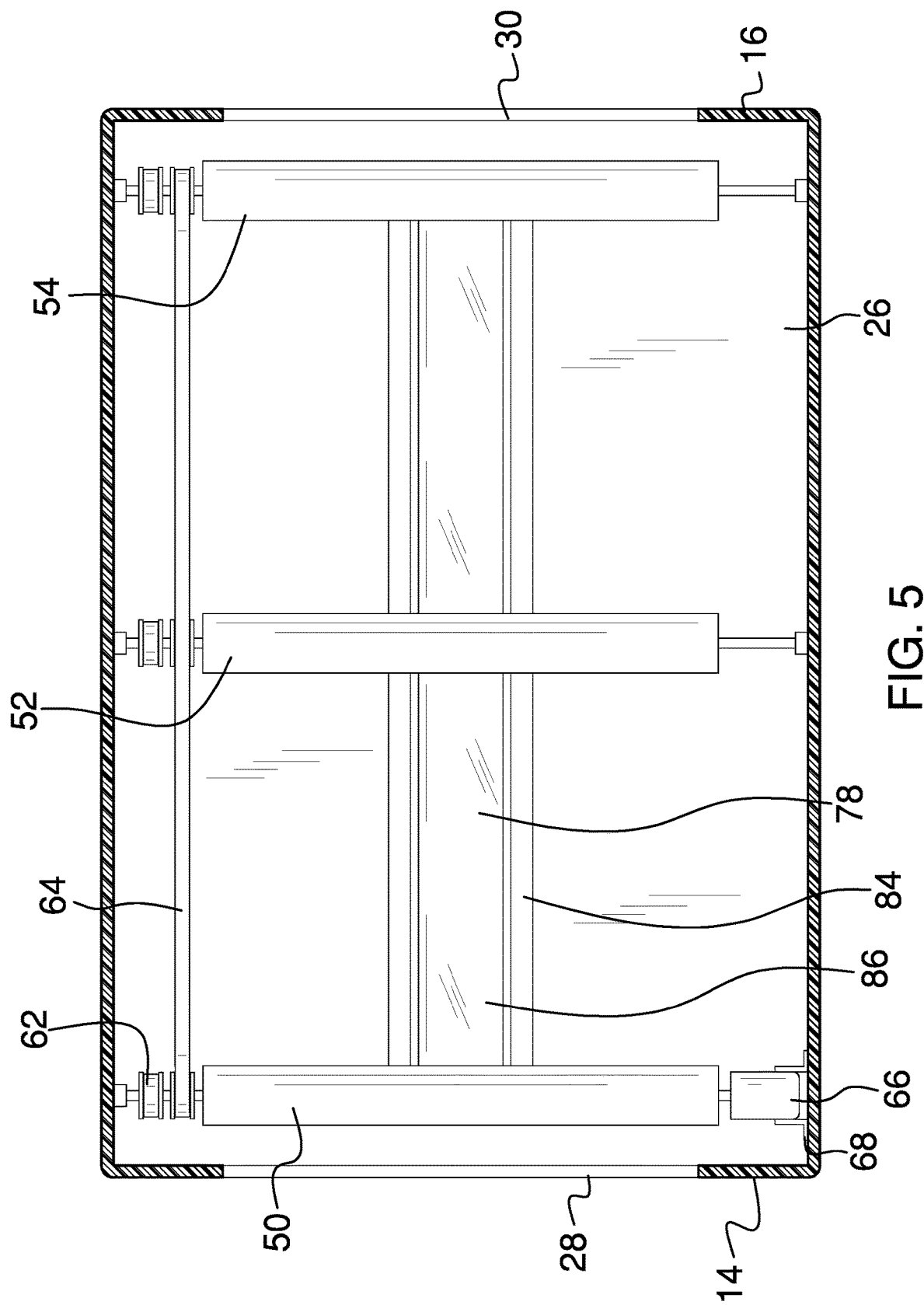
FIG. 5 is a cross-sectional view of an embodiment of the disclosure along the line 5-5 of FIG. 2.

With reference now to the drawings, and in particular to FIGS. 1 through 6 thereof, a new banknote sanitizer embodying the principles and concepts of an embodiment of the disclosure and generally designated by the reference numeral 10 will be described.

As best illustrated in FIGS. 1 through 6, the paper money sanitation apparatus 10 generally comprises a housing 12 having a housing front side 14, a housing back side 16, a housing top side 18, a housing bottom side 20, a housing left side 22, and a housing right side 24 defining a housing cavity 26. The housing 12 has an input slot 28 extending through to the housing cavity 26 and the housing back side 16 has an output slot 30 extending through to the housing cavity 26. The input slot 28 and the output slot 30 are configured to pass a standard banknote 32. The housing 12 may be rectangular prismatic and utilized on a countertop to facilitate the passing of the banknote 32 from one person to another across the countertop.

The input slot 28 may extend through the housing front side 14 and lie coplanar with the output slot 30 as shown in FIGS. 1-5. The input slot 28 may alternatively lie within a cavity 34 of the housing top side. The cavity 34 is configured to hold a stack of banknotes 32 and may have a sloped cavity bottom side 36 to assist feeding the banknote 32 into the input slot 28. A lid 38 may be hingingly coupled to the housing top side 18 to selectively cover and uncover the cavity 34.

Figure 6:
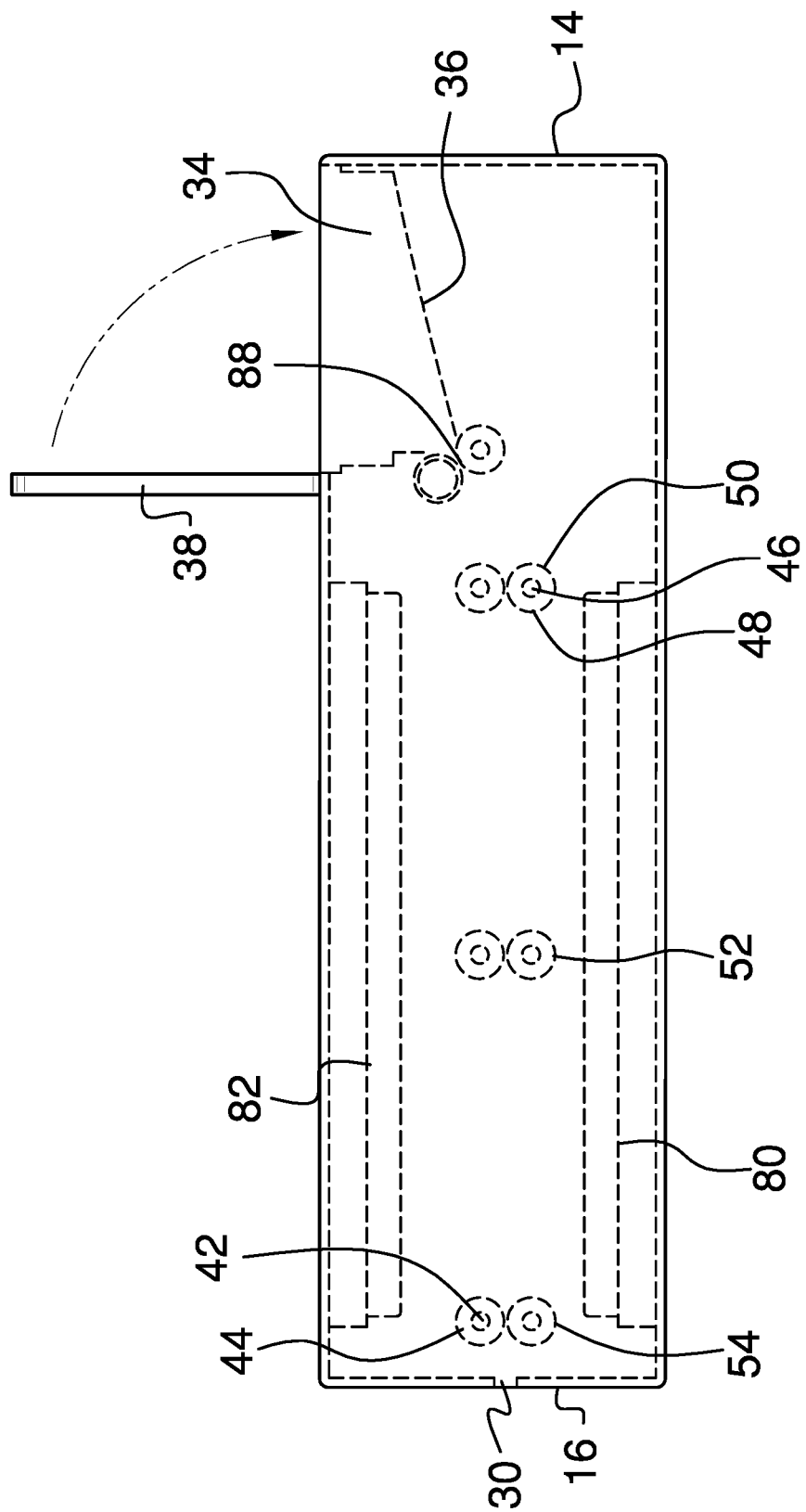
FIG. 6 is a side elevation view of an embodiment of the disclosure.

A plurality of roller pairs 40 is coupled to the housing 12. Each roller pair 40 comprises an upper roller axle 42 extending between the housing left side 22 and the housing right side 24 within the housing cavity 26. An upper roller bar 44 is coupled to the upper roller axle 42. A lower roller axle 46 extends between the housing left side 22 and the housing right side 24 within the housing cavity 26 vertically beneath the upper roller axle 42. A lower roller bar 48 is coupled to the lower roller axle 46. The upper roller bar 44 and the lower roller bar 48 are positioned to have sufficient space to contactingly receive the banknote 32 and pass the banknote 32 to the adjacent roller pair 40 and ultimately out of the output slot 30. The plurality of roller pairs 40 may be a set of three evenly spaced roller pairs 40 including a front roller pair 50, a medial roller pair 52, and a back roller pair 54. When the input slot 28 lies in the cavity 34 there may be an additional roller pair 40 adjacent the input slot 28 that is angled to match the slope of the cavity bottom side 36 as seen in FIG. 6.

A drive system 56 is coupled to the plurality of roller pairs 40. The drive system 56 is in operational communication with each of the upper roller axles 42 and the lower roller axles 46 to synchronize rotation thereof. The drive system 56 may include a plurality of gears 58 coupled to the upper roller axle 42 and the lower roller axle 46 of each roller pair and a plurality of belts 60 coupled between the plurality of gears 58. The plurality of belts 60 may include a plurality of vertical belts 62 connecting the gears of the plurality of gears 58 coupled to the upper roller axle 42 and the lower roller axle 46 of each roller pair and a horizontal belt 64 connecting the gears of the plurality of gears 52 coupled to the upper roller axle 42 of each roller pair.

A motor 66 is coupled to the drive system 56 and is in operational communication with the drive system 66 to rotate the plurality of roller pairs 40. The motor 66 may have a motor mount 68 coupled to the housing right side 24 in line with the upper roller axle 42 of the roller pair 40 closest to the input slot 28. A power button 70 is coupled to the housing 12 and is in operational communication with the motor 66. The power button 70 may include a button mount 72 coupled to the housing top side 18 and a rocker switch 74 coupled to the button mount 72. A battery 76 is coupled to the housing 12 and is in operational communication with the motor 66.

A plurality of ultraviolet lights 78 is coupled to the housing 12. Each ultraviolet light 78 is coupled within the housing cavity 26 and is in operational communication with the battery 76. The plurality of ultraviolet lights 78 may include a lower light 80 coupled to the housing bottom side 20 and an upper light 82 coupled to the housing top side 18 to sanitize both sides of the banknote 32 as it passes therebetween. Each of the ultraviolet lights 78 may include a flanged light housing 84 coupled to the housing 12 and a cylindrical bulb 86 coupled within the light housing 84. Each ultraviolet light 78 is oriented perpendicularly to the housing front side 14 and the housing back side 16 to maximize exposure to the banknote 32.

In use, the power button 70 is activated to rotate the plurality of roller pairs 40 and the plurality of ultraviolet lights 78. The banknote 32 is then placed into the input slot 28 and retrieved from the output slot 30 after being sanitized by the plurality of ultraviolet lights 78.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A paper money sanitation apparatus comprising:
    a housing having a housing front side, a housing back side, a housing top side, a housing bottom side, a housing left side, and a housing right side defining a housing cavity, the housing having an input slot extending through to the housing cavity and the housing back side having an output slot extending through to the housing cavity;
    a plurality of roller pairs coupled to the housing, each roller pair comprising:
        an upper roller axle extending between the housing left side and the housing right side within the housing cavity;
        an upper roller bar coupled to the upper roller axle;
        a lower roller axle extending between the housing left side and the housing right side within the housing cavity vertically beneath the upper roller axle; and
        a lower roller bar coupled to the lower roller axle, the upper roller bar and the lower roller bar being positioned to have sufficient space to contactingly receive a banknote;
    a drive system coupled to the plurality of roller pairs, the drive system being in operational communication with each of the upper roller axles and the lower roller axles to synchronize rotation thereof;
    a motor coupled to the drive system, the motor being in operational communication with the drive system to rotate the plurality of roller pairs;
    a power button coupled to the housing, the power button being in operational communication with the motor;
    a battery coupled to the housing, the battery being in operational communication with the motor; and
    a plurality of ultraviolet lights coupled to the housing, each ultraviolet light being coupled within the housing cavity and being in operational communication with the battery;

the drive system including a plurality of gears coupled to the upper roller axle and the lower roller axle of each roller pair and a plurality of belts coupled between the plurality of gears.

2. The paper money sanitation apparatus of claim 1 further comprising the input slot extending through the housing front side and being coplanar with the output slot; each of the plurality of roller pairs being arranged in parallel.

3. The paper money sanitation apparatus of claim 1 further comprising the plurality of belts including a plurality of vertical belts connecting the gears of the plurality of gears coupled to the upper roller axle and the lower roller axle of each roller pair and a horizontal belt connecting the gears of the plurality of gears coupled to the upper roller axle of each roller pair.

4. The paper money sanitation apparatus of claim 1 further comprising the input slot being within a cavity of the housing top side, the cavity having a sloped cavity bottom side.

5. The paper money sanitation apparatus of claim 1 further comprising a lid hingingly coupled to the housing top side to selectively cover and uncover the cavity.

6. A paper money sanitation apparatus comprising:
a housing having a housing front side, a housing back side, a housing top side, a housing bottom side, a housing left side, and a housing right side defining a housing cavity, the housing having an input slot extending through to the housing cavity and the housing back side having an output slot extending through to the housing cavity;
a plurality of roller pairs coupled to the housing, each roller pair comprising:
an upper roller axle extending between the housing left side and the housing right side within the housing cavity;
an upper roller bar coupled to the upper roller axle;
a lower roller axle extending between the housing left side and the housing right side within the housing cavity vertically beneath the upper roller axle; and
a lower roller bar coupled to the lower roller axle, the upper roller bar and the lower roller bar being positioned to have sufficient space to contactingly receive a banknote;
a drive system coupled to the plurality of roller pairs, the drive system being in operational communication with each of the upper roller axles and the lower roller axles to synchronize rotation thereof;
a motor coupled to the drive system, the motor being in operational communication with the drive system to rotate the plurality of roller pairs:
a power button coupled to the housing, the power button being in operational communication with the motor;
a battery coupled to the housing, the battery being in operational communication with the motor;
a plurality of ultraviolet lights coupled to the housing, each ultraviolet light being coupled within the housing cavity and being in operational communication with the battery; and
the plurality of roller pairs being a set of three evenly spaced roller pairs including a front roller pair, a medial roller pair, and a back roller pair.

7. The paper money sanitation apparatus of claim 6 further comprising the motor being in operational communication with drive system connected to the upper roller axle of the front roller pair.

8. A paper money sanitation apparatus comprising:
a housing having a housing front side, a housing back side, a housing top side, a housing bottom side, a housing left side, and a housing right side defining a housing cavity, the housing having an input slot extending through to the housing cavity and the housing back side having an output slot extending through to the housing cavity;
a plurality of roller pairs coupled to the housing, each roller pair comprising:
an upper roller axle extending between the housing left side and the housing right side within the housing cavity;
an upper roller bar coupled to the upper roller axle;
a lower roller axle extending between the housing left side and the housing right side within the housing cavity vertically beneath the upper roller axle; and
a lower roller bar coupled to the lower roller axle, the upper roller bar and the lower roller bar being positioned to have sufficient space to contactingly receive a banknote;
a drive system coupled to the plurality of roller pairs, the drive system being in operational communication with each of the upper roller axles and the lower roller axles to synchronize rotation thereof;
a motor coupled to the drive system, the motor being in operational communication with the drive system to rotate the plurality of roller pairs;
a power button coupled to the housing, the power button being in operational communication with the motor;
a battery coupled to the housing, the battery being in operational communication with the motor;
a plurality of ultraviolet lights coupled to the housing, each ultraviolet light being coupled within the housing cavity and being in operational communication with the battery; and
the plurality of ultraviolet lights including a lower light coupled to the housing bottom side and an upper light coupled to the housing top side.

9. The paper money sanitation apparatus of claim 8 further comprising each of the ultraviolet lights including a flanged light housing coupled to the housing and a cylindrical bulb coupled within the light housing, each ultraviolet light being oriented perpendicularly to the housing front side and the housing back side.

10. A paper money sanitation apparatus comprising:
a housing having a housing front side, a housing back side, a housing top side, a housing bottom side, a housing left side, and a housing right side defining a housing cavity, the housing having an input slot extending through to the housing cavity and the housing back side having an output slot extending through to the housing cavity, the input slot being within a cavity of the housing top side, the cavity having a sloped cavity bottom side;
a lid hingingly coupled to the housing top side to selectively cover and uncover the cavity;
a plurality of roller pairs coupled to the housing, each roller pair comprising:
an upper roller axle extending between the housing left side and the housing right side within the housing cavity;
an upper roller bar coupled to the upper roller axle;
a lower roller axle extending between the housing left side and the housing right side within the housing cavity vertically beneath the upper roller axle; and a lower roller bar coupled to the lower roller axle, the upper roller bar and the lower roller bar being positioned to have sufficient space to contactingly receive a banknote;

wherein the plurality of roller pairs is a set of three evenly spaced roller pairs including a front roller pair, a medial roller pair, and a back roller pair;

a drive system coupled to the plurality of roller pairs, the drive system being in operational communication with each of the upper roller axles and the lower roller axles to synchronize rotation thereof, the drive system including a plurality of gears coupled to the upper roller axle and the lower roller axle of each roller pair and a plurality of belts coupled between the plurality of gears, the plurality of belts including a plurality of vertical belts connecting the gears of the plurality of gears coupled to the upper roller axle and the lower roller axle of each roller pair and a horizontal belt connecting the gears of the plurality of gears coupled to the upper roller axle of each roller pair;

a motor coupled to the drive system, the motor being in operational communication with the drive system to rotate the plurality of roller pairs;

a power button coupled to the housing, the power button being in operational communication with the motor;

a battery coupled to the housing, the battery being in operational communication with the motor; and a plurality of ultraviolet lights coupled to the housing, each ultraviolet light being coupled within the housing cavity and being in operational communication with the battery, the plurality of ultraviolet lights including a lower light coupled to the housing bottom side and an upper light coupled to the housing top side, each of the ultraviolet lights including a flanged light housing coupled to the housing and a cylindrical bulb coupled within the light housing, each ultraviolet light being oriented perpendicularly to the housing front side and the housing back side.

11. A paper money sanitation apparatus comprising:

a housing having a housing front side, a housing back side, a housing top side, a housing bottom side, a housing left side, and a housing right side defining a housing cavity, the housing having an input slot extending through to the housing cavity and the housing back side having an output slot extending through to the housing cavity, the input slot extending through the housing front side and being coplanar with the output slot;

a plurality of roller pairs coupled to the housing, each roller pair comprising:
an upper roller axle extending between the housing left side and the housing right side within the housing cavity;
an upper roller bar coupled to the upper roller axle;
a lower roller axle extending between the housing left side and the housing right side within the housing cavity vertically beneath the upper roller axle; and
a lower roller bar coupled to the lower roller axle, the upper roller bar and the lower roller bar being positioned to have sufficient space to contactingly receive a banknote;
wherein the plurality of roller pairs is a set of three evenly spaced roller pairs including a front roller pair, a medial roller pair, and a back roller pair, each of the plurality of roller pairs being arranged in parallel;

a drive system coupled to the plurality of roller pairs, the drive system being in operational communication with each of the upper roller axles and the lower roller axles to synchronize rotation thereof, the drive system including a plurality of gears coupled to the upper roller axle and the lower roller axle of each roller pair and a plurality of belts coupled between the plurality of gears, the plurality of belts including a plurality of vertical belts connecting the gears of the plurality of gears coupled to the upper roller axle and the lower roller axle of each roller pair and a horizontal belt connecting the gears of the plurality of gears coupled to the upper roller axle of each roller pair;

a motor coupled to the drive system, the motor being in operational communication with the drive system to rotate the plurality of roller pairs;

a power button coupled to the housing, the power button being in operational communication with the motor;

a battery coupled to the housing, the battery being in operational communication with the motor; and a plurality of ultraviolet lights coupled to the housing, each ultraviolet light being coupled within the housing cavity and being in operational communication with the battery, the plurality of ultraviolet lights including a lower light coupled to the housing bottom side and an upper light coupled to the housing top side, each of the ultraviolet lights including a flanged light housing coupled to the housing and a cylindrical bulb coupled within the light housing, each ultraviolet light being oriented perpendicularly to the housing front side and the housing back side.

\* \* \* \* \*